US008358406B2

(12) United States Patent
Ikota et al.

(10) Patent No.: US 8,358,406 B2
(45) Date of Patent: Jan. 22, 2013

(54) DEFECT INSPECTION METHOD AND DEFECT INSPECTION SYSTEM

(75) Inventors: Masami Ikota, Higashiyamoto (JP); Tomohiro Funakoshi, Hitachinaka (JP); Shigeaki Hijikata, Ome (JP)

(73) Assignee: Hitachi High-Technologies Corporation, Tokyo (JP)

( * ) Notice: Subject to any disclaimer, the term of this patent is extended or adjusted under 35 U.S.C. 154(b) by 247 days.

(21) Appl. No.: 12/350,463

(22) Filed: Jan. 8, 2009

(65) Prior Publication Data
US 2009/0180109 A1 Jul. 16, 2009

(30) Foreign Application Priority Data

Jan. 11, 2008 (JP) ................................ 2008-003801

(51) Int. Cl.
*G01N 21/00* (2006.01)

(52) U.S. Cl. .................. 356/237.1; 250/205; 356/237.2; 356/237.6

(58) Field of Classification Search .... 356/237.1–237.5; 250/205
See application file for complete search history.

(56) References Cited

U.S. PATENT DOCUMENTS

| 3,436,556 | A | * | 4/1969 | McCartney | 250/223 R |
| 5,717,485 | A | * | 2/1998 | Ito et al. | 356/237.1 |
| 6,404,498 | B1 | * | 6/2002 | Maeda et al. | 356/394 |
| 6,643,007 | B2 | * | 11/2003 | Le | 356/237.3 |
| 6,886,153 | B1 | | 4/2005 | Bevis | |
| 7,037,735 | B2 | * | 5/2006 | Noguchi et al. | 438/18 |
| 7,180,584 | B2 | * | 2/2007 | Maeda et al. | 356/237.2 |
| 7,465,935 | B2 | | 12/2008 | Urano et al. | |
| 7,508,973 | B2 | | 3/2009 | Okabe et al. | |
| 7,528,942 | B2 | * | 5/2009 | Nakano et al. | 356/237.3 |
| 2002/0044278 | A1 | * | 4/2002 | Le | 356/237.3 |
| 2002/0154303 | A1 | * | 10/2002 | Maeda et al. | 356/394 |
| 2006/0215901 | A1 | | 9/2006 | Nakagaki et al. | |

(Continued)

FOREIGN PATENT DOCUMENTS

JP 5-045862 2/1993
JP 2005-17159 A 1/2005

(Continued)

OTHER PUBLICATIONS

Japanese Office Action with English translation issued in Japanese Application No. 2008-003801 issued on Apr. 24, 2012.

*Primary Examiner* — Tarifur Chowdhury
*Assistant Examiner* — Isiaka Akanbi
(74) *Attorney, Agent, or Firm* — McDermott Will & Emery LLP

(57) ABSTRACT

An object of the invention is to provide a defect inspection method which can prevent the failure in detecting a defect, caused by saturation of a pattern signal obtained by inspecting an inspected object, so that the investigation of the cause for defect occurrence can be done earlier. To achieve this object, according to an embodiment of the invention, there is provided a defect inspection that irradiates laser light on an inspected object having a pattern formed thereon, detects a signal from the inspected object and thereby detects a defect, the inspection including: inputting pattern information contained in layout data on the inspected object; determining based on the inputted pattern information, at least one of arrangement, repetitiveness and density for each of a plurality of inspected areas of the inspected object; estimating a saturation level of the detected signal based on the determination result; and determining a transmittance condition so that the signal does not saturate.

10 Claims, 11 Drawing Sheets

U.S. PATENT DOCUMENTS

| | | |
|---|---|---|
| 2006/0288325 A1 | 12/2006 | Miyamoto et al. |
| 2007/0011519 A1 | 1/2007 | Takeda et al. |
| 2007/0070336 A1* | 3/2007 | Maeda et al. .............. 356/237.2 |
| 2007/0206184 A1 | 9/2007 | Uto et al. |

FOREIGN PATENT DOCUMENTS

| | | |
|---|---|---|
| JP | 2005-514774 | 5/2005 |
| JP | 2006-201044 A | 8/2006 |
| JP | 2006-269489 | 10/2006 |
| JP | 2007-003306 | 1/2007 |
| JP | 2007-232555 | 9/2007 |
| JP | 2006-351746 | 12/2008 |

* cited by examiner

Defect inspection apparatus 9

(A)

(B)

(C)

(A)

(B)

(C)

DEFECT INSPECTION METHOD AND DEFECT INSPECTION SYSTEM

BACKGROUND OF THE INVENTION

1. Field of the Invention

The present invention relates to a defect inspection method and defect inspection system for detecting a foreign matter or pattern defect in a semiconductor wafer, a photomask, a magnetic disk, a liquid crystal substrate or the like.

2. Background Art

In the process of fabricating semiconductor devices, a foreign matter or occurrence of a defect or the like in a circuit pattern results in a defective product. This is also the case with a magnetic disk and a liquid crystal substrate. Further, in the case of a photomask used to form patterns in a semiconductor wafer or a liquid crystal substrate, also, the presence of a defect causes wrong patterns to be formed in the semiconductor wafer or liquid crystal substrate, thus resulting in a defective product.

Descriptions will be given below by taking semiconductor wafer as an example. In inspecting a semiconductor wafer for defective appearance caused by a foreign matter or defective circuit pattern, the defective appearance must be quantified to check at all times the occurrence of a problem in the fabricating equipment or fabricating environment. Further, the shape of defective appearance is observed to check whether the defective appearance exerts critical effects in the product, whereby the degree of effect by the defective appearance can be determined. Instead of determining from the image of defective appearance by visual inspection whether or not the defective appearance is critical, there has recently been introduced a technique of ADC (Automatic Defect Classification) that automatically classifies the defective appearance (for example, refer to JP Patent Publication (Kokai) No. 2006-269489A).

As the defective appearance inspection apparatus, there is known an optical pattern inspection apparatus using a dark-field optical microscope (for example, refer to JP Patent Publication (Kokai) No. 05-45862A). The defect inspection mechanism which inspects a semiconductor wafer will be briefly described below. Chips constituting multiple semiconductor devices are formed on a single semiconductor wafer. These inspected chips are each typically constituted of a group of multiple patterns based on the functions of the memory area, peripheral circuit area, logic area and the like. When laser light is irradiated on the inspected object, the incident light is diffracted by the patterns, but the incident light irradiated on a defect is scattered by the defect. The diffracted light and scattered light pass through a field lens of the inspection apparatus and are adjusted to an appropriate light intensity by a variable-transmittance filter. Thereafter, the diffracted light from a pattern having a high repetitiveness such as a memory area pattern is eliminated by a spatial filter. However, the diffracted light from a pattern having a low repetitiveness such as a peripheral circuit area pattern or logic circuit area pattern, and the scattered light from a defect, which are not eliminated by the spatial filter, enters a signal detector and the signals are stored in the memory of the inspection apparatus. Then, a difference between the diffracted light signal and scattered light signal and a reference chip signal preinstalled in the memory is calculated by a difference circuit, and the difference signal is compared with a predetermined threshold level by a comparator, so that the signal greater than the threshold level is detected as a defect signal.

SUMMARY OF THE INVENTION

Diffracted light produced, as described above, when laser is irradiated on an inspected object depends greatly on pattern repetitiveness and pattern density. While the signal from a high-repetitiveness pattern is effectively eliminated by the spatial filter, the signal from a low-repetitiveness pattern such as a logic circuit pattern or peripheral circuit pattern is not eliminated by the spatial filter and enters the signal detector, thus causing detection signal saturation. When detection signal saturation occurs, the defect signal cannot be separated, so that the defect cannot be detected. In order to address this problem, a method can be used which uses multiple detectors having different saturation levels, but this method takes high cost. There can also be used a method which performs multiple inspections under different optical conditions for each area with respect to spatial filter, laser power, signal transmittance and the like, and combines the inspection results; but this method results in low throughput and it also takes much labor and time to optimize the multiple conditions, and it is difficult to learn the operation method easily. Further, the high sensitivity of the inspection apparatus makes the image data voluminous, and it takes much time to sort out the data to check detected defects, thus posing a large problem.

An object of the present invention is to provide a defect inspection apparatus and defect inspection method which can prevent the failure in detecting a defect, caused by saturation of a pattern signal obtained by inspecting an inspected object, so that the investigation of the cause for defect occurrence can be done earlier.

To achieve this object, according to an embodiment of the invention, there is provided a defect inspection that irradiates laser light on an inspected object having a pattern formed thereon, detects a signal from the inspected object and thereby detects a defect, the inspection including: inputting pattern information contained in layout data on the inspected object; determining based on the inputted pattern information, at least one of arrangement, repetitiveness and density for each of a plurality of inspected areas of the inspected object; estimating a saturation level of the detected signal based on the determination result; and determining a transmittance condition so that the signal does not saturate.

According to the present invention, there can be provided a defect inspection apparatus and defect inspection method which can prevent the failure in detecting a defect, caused by saturation of a pattern signal obtained by inspecting an inspected object, so that the investigation of the cause for defect occurrence can be done earlier.

DETAILED DESCRIPTION OF THE PREFERRED EMBODIMENTS

Figure 1:
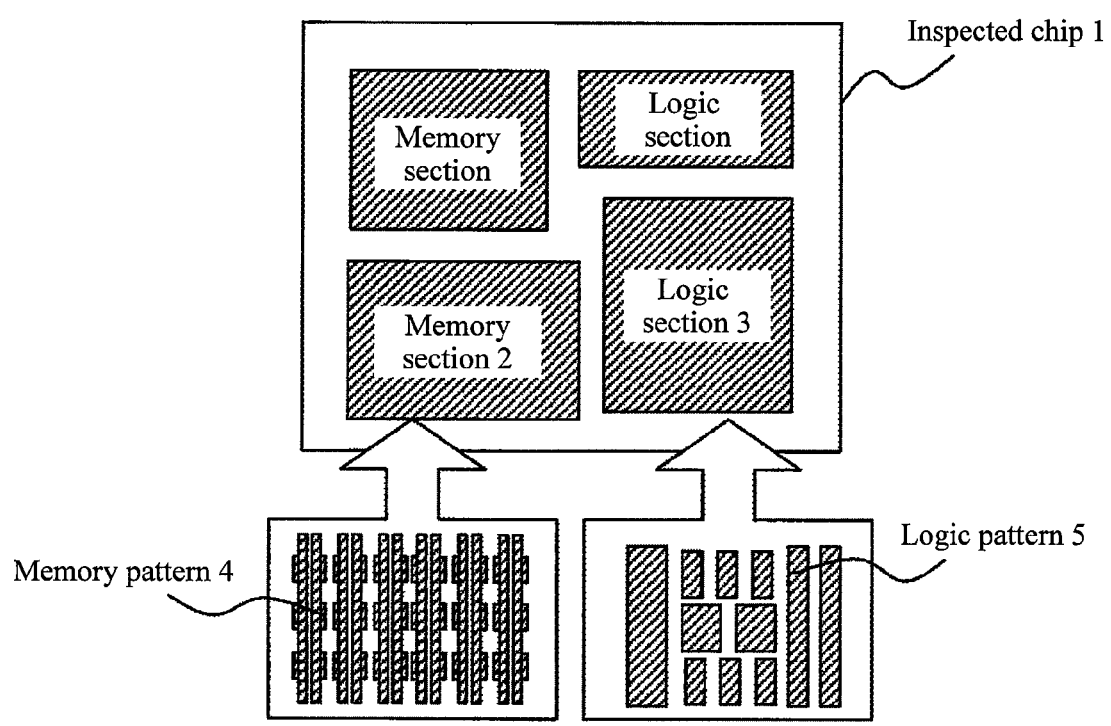
FIG. 1 is a plan view illustrating an example of pattern arrangement in an inspected chip.

FIG. 1 is a plan view illustrating an example of pattern arrangement in an inspected chip. An inspected chip 1 is typically constituted of a memory section 2, logic section 3 and the like provided for each function; these sections are connected via wires. Usually, a memory pattern 4 has a high-repetitiveness, dense pattern configuration; and a logic pattern 5 has a low-repetitiveness pattern configuration.

Figure 2:
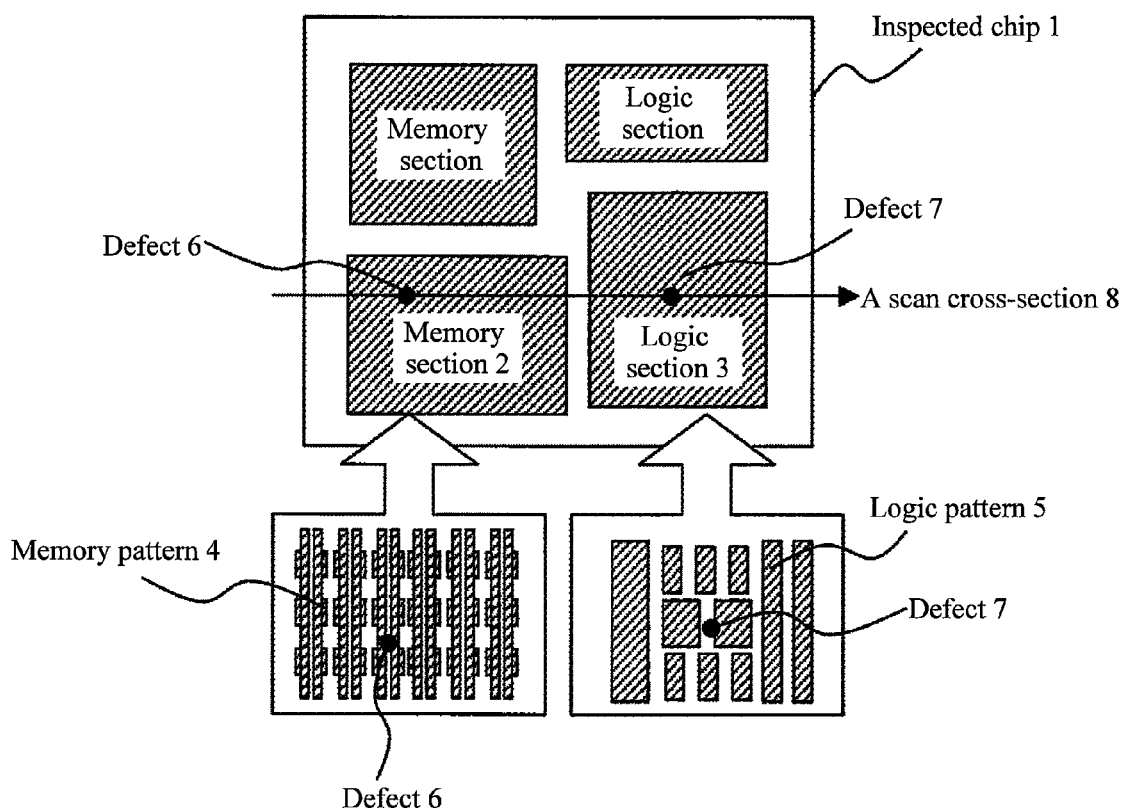
FIG. 2 is a schematic view illustrating a pattern and defect in the inspected chip.
Figure 3:
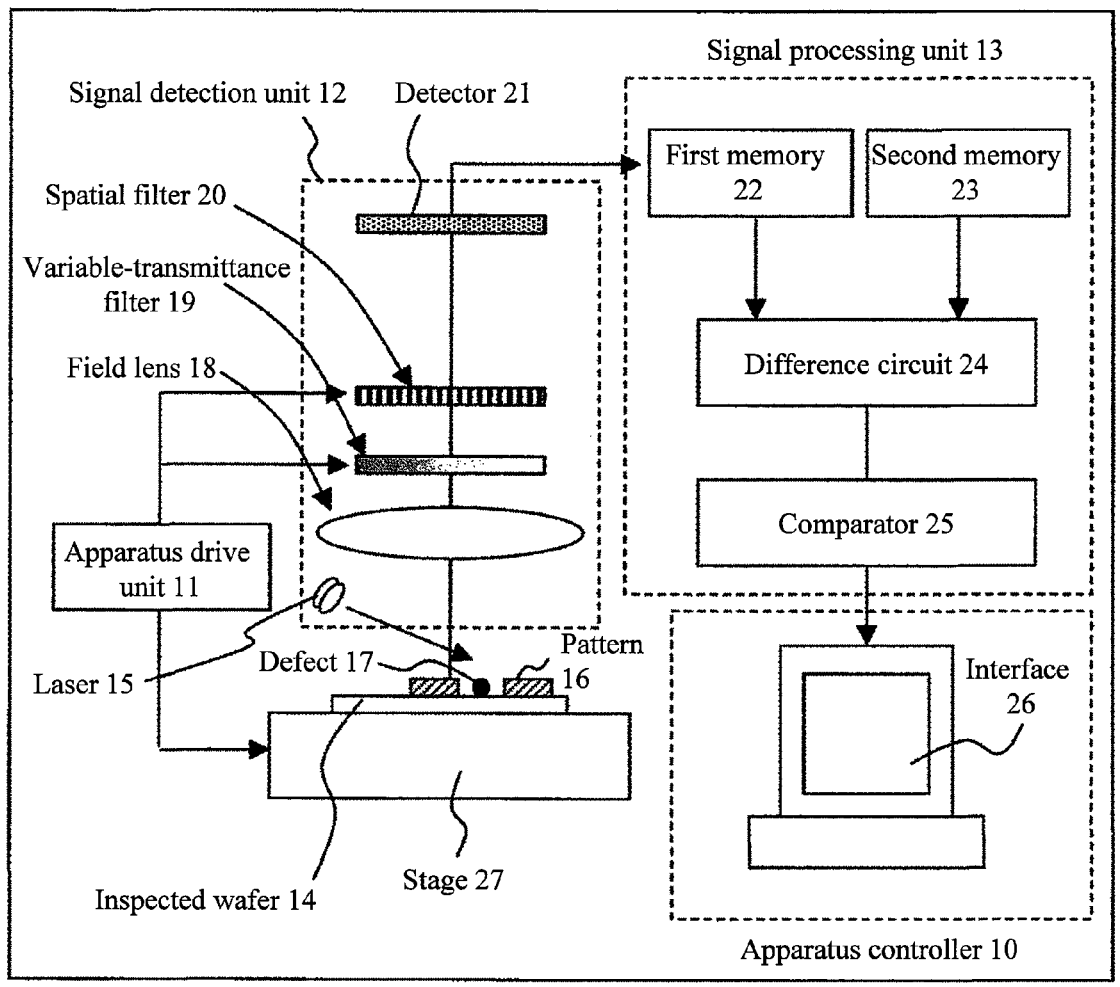
FIG. 3 is a system configuration diagram of a related art defect inspection apparatus.

A defect inspection method will be described with reference to FIGS. 2, 3 and 4. FIG. 2 is a schematic view illustrating a pattern and defect in the inspected chip 1. Now, assume that there is a defect 6 on the memory pattern 4, and a defect 7 on the logic pattern 5. FIG. 3 is a system configuration diagram of a defect inspection apparatus. The defect inspection apparatus 9 mainly includes an apparatus controller 10, apparatus drive unit 11, signal detection unit 12, signal processing unit 13 and stage 27. When a laser 15 is irradiated on an inspected wafer 14 on the stage 27, the incident light is diffracted by a pattern 16, but when irradiated on a defect 17, the incident light is scattered. The diffracted light and scattered light pass through a field lens 18, and are adjusted to a given light intensity by a variable-transmittance filter 19. Thereafter, the diffracted light from a pattern having a high repetitiveness such as the memory area pattern is eliminated by a spatial filter 20. However, the diffracted light from a pattern having a low repetitiveness such as the peripheral circuit area pattern or logic circuit area pattern, and the scattered light from the defect, which are not eliminated by the spatial filter, enters a signal detector 21 and the signals are stored in a first memory 22 of the signal processing unit 13. Then, a difference between the diffracted light signal and scattered light signal and a reference chip signal preinstalled in a second memory 23 is calculated by a difference circuit, and the difference signal is compared with a predetermined threshold level by a comparator 25, so that the signal greater than the threshold level is detected as a defect signal. The detection result is displayed on an interface 26 of the apparatus controller 10. This laser scan is applied to the whole inspection area by driving the stage 27 by means of the apparatus drive unit 11.

Figure 4:
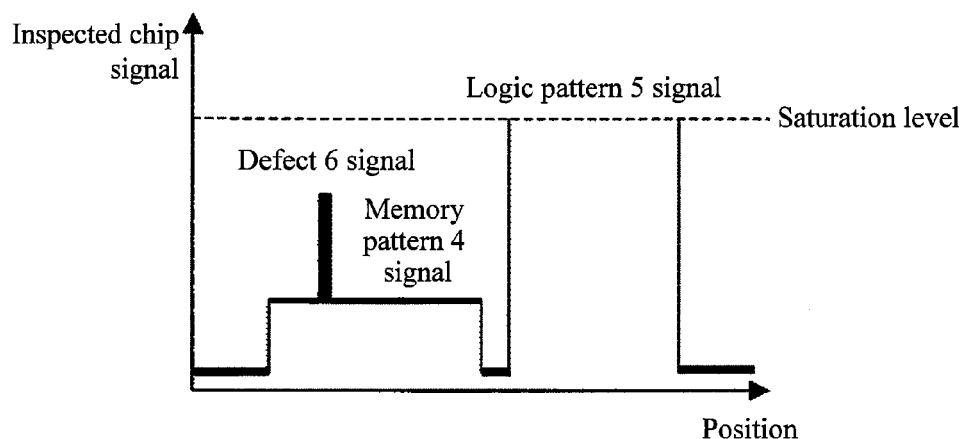
FIG. 4 is a graph illustrating a signal level at the A scan cross-section of FIG. 2.
Figure 4:
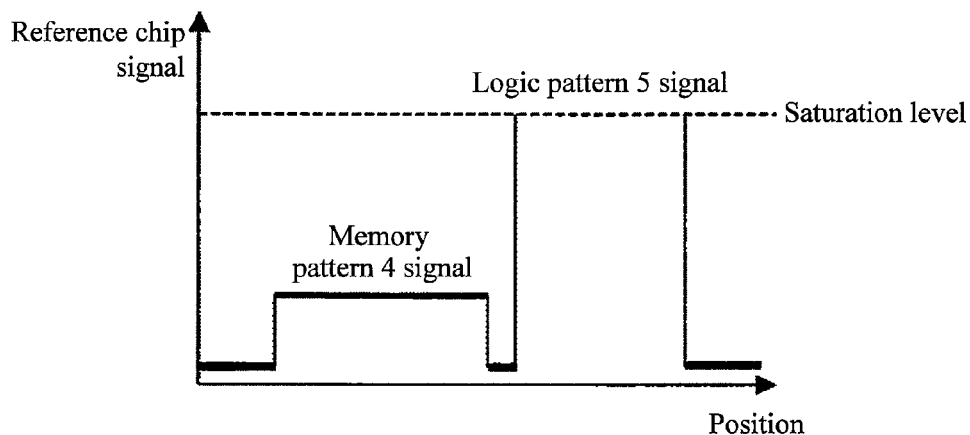
Figure 4:
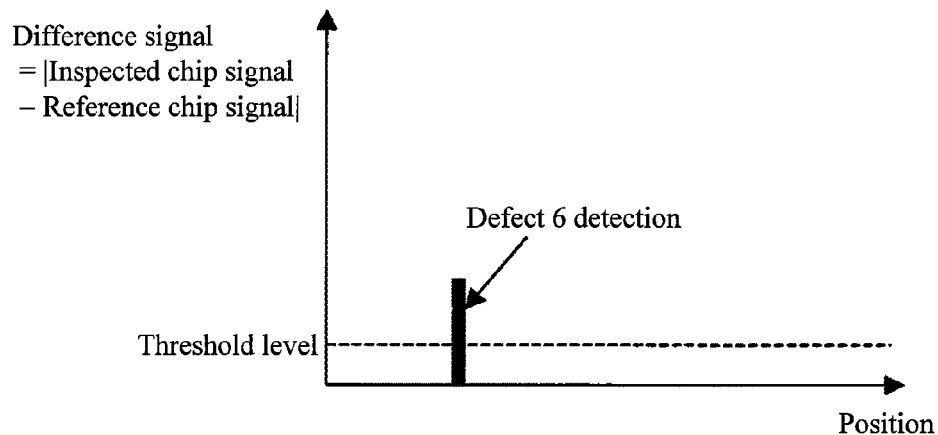

FIG. 4 is a graph illustrating a signal level at the A scan cross-section 8 of FIG. 2; the position is plotted along the abscissa and the signal level along the ordinate. In the case of a high-repetitiveness pattern such as the memory pattern 4, the signal is effectively eliminated by the spatial filter 20. However, in the case of a low-repetitiveness pattern such as the logic pattern 5, the spatial filter 20 is ineffective, and thus the pattern signal is not sufficiently eliminated, so that the detector 21 saturates. Consequently, the defect 6 in the memory section 2 can be detected but the defect 7 in the logic section 3 cannot be detected.

In FIG. 4(A), the signal from the inspected chip is plotted along the ordinate. Since the detection signal from the memory pattern 4 in the memory section 2 of FIG. 2 does not reach the saturation level, the signal from the defect 6 appears. However, since the signal from the logic pattern 5 in the logic section 3 of FIG. 2 exceeds the saturation level, the signal from the defect 7 does not appear. In FIG. 4(B), the signal from a reference chip is plotted along the ordinate. As in FIG. 4(A), the detection signal from the memory pattern 4 in the memory section 2 of FIG. 2 does not reach the saturation level, but the signal from the logic pattern 5 in the logic section 3 of FIG. 2 exceeds the saturation level. In FIG. 4(C), the difference signal, i.e., the difference between the inspected chip signal of FIG. 4(A) and the reference chip signal of FIG. 4(B) is plotted along the ordinate. As illustrated in FIG. 4(C), the signal from the memory pattern 4 in the memory section 2 of FIG. 2 disappears as a result of calculating the difference, and only the signal from the defect 6 illustrated in FIG. 4(A) can be observed; if this signal exceeds the threshold level, the defect 6 can be detected. However, the signal from the logic pattern 5 in the logic section 3 saturates and the signal from the defect 7 does not appear, so the defect 7 cannot be detected by calculating the difference.

Figure 5:
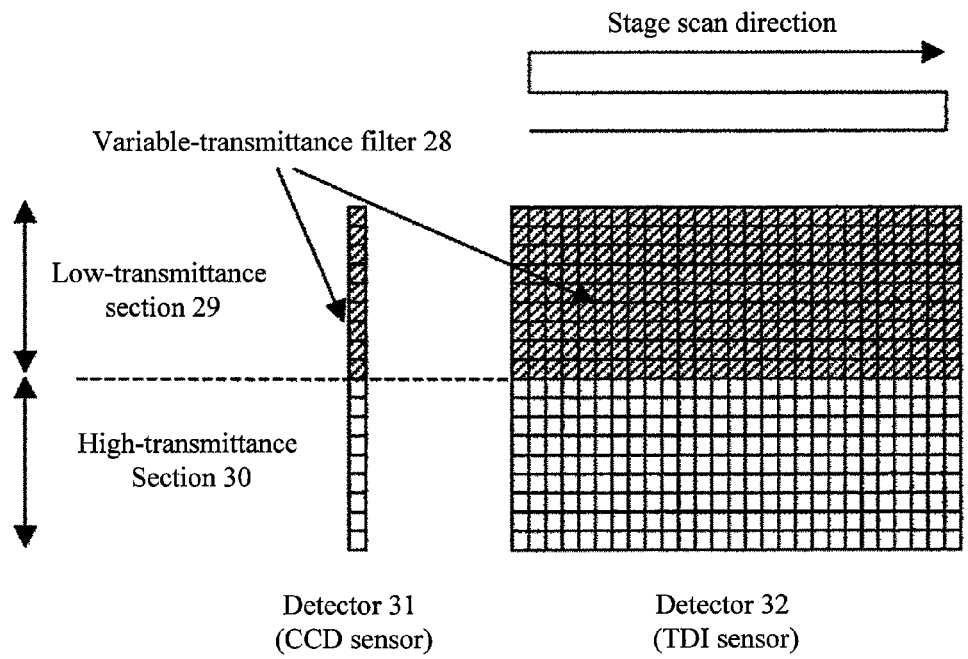
FIG. 5 is a schematic configuration diagram of a detector, for which the transmittance is variable, used by the present invention.

FIG. 5 is a schematic configuration diagram of a detector, for which the transmittance is variable, used by the present invention. As the detector 21 illustrated in FIG. 3, there are provided a detector 31 and detector 32. The detector 31 is a CCD (Charge Coupled Devices) sensor, and the detector 32 is a TDI (Time Delay and Integration) sensor. To arrange a low-transmittance section 29 in one half of the sensor surface and a high-transmittance section 30 in the other half of the sensor surface, there is provided a variable-transmittance filter 28.

Figure 6:
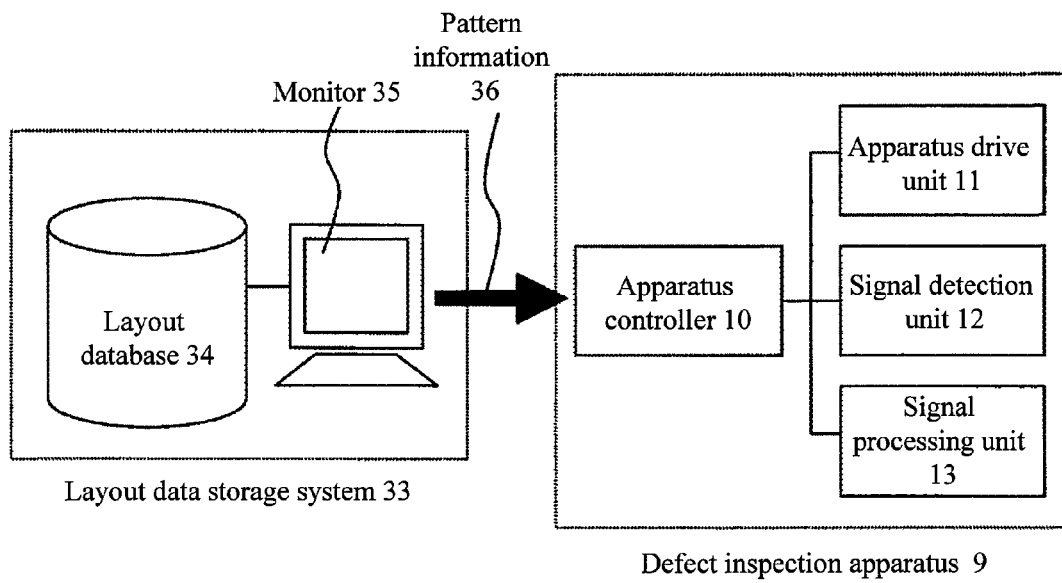
FIG. 6 is a schematic configuration diagram of a defect inspection system according to the present invention.

FIG. 6 is a system configuration diagram of a defect inspection system according to the present invention. A layout data storage system 33 is connected to the defect inspection apparatus 9 illustrated in FIG. 3. The layout data storage system 33 includes a layout database 34 and a monitor 35 with a microprocessor. The defect inspection apparatus 9 includes the apparatus controller 10 with a microprocessor, and the apparatus drive unit 11, signal detection unit 12 and signal processing unit 13. The apparatus controller 10 stores inspection condition information such as information on the inspected chip 1, laser power, spatial filter 20 configuration and the transmittance of the variable-transmittance filter 19. The apparatus drive unit 11 drives based on the information stored in the apparatus controller 10, the driven sections such as the stage 27, variable-transmittance filter 19 and spatial filter 20. The signal detection unit 12 includes the laser 15, field lens 18, variable-transmittance filter 19, spatial filter 20, detector 21 and the like, and detects a pattern signal and defect signal. The signal processing unit 13 includes an image processing substrate and the like, and distinguishes the defects 6 and 7 from the patterns. Pattern information 36 including the pattern arrangement, pattern configuration and the like in the inspected chip is sent from the layout data storage system 33 to the apparatus controller 10 of the defect inspection apparatus 9. The apparatus controller 10 determines the pattern repetitiveness and density based on the pattern information 36. In driving the stage 27 by means of the apparatus drive unit 11 to inspect the inspected area, the spatial filter 20 is effective for a pattern area determined to have a high repetitiveness, so the signal from the high-transmittance section 30 of the detector 31 or 32 illustrated in FIG. 5 is used. For a pattern area determined to have a low repetitiveness, the signal from the low-transmittance section 29 of the detector 31 or 32 is used. These signals are compared with the threshold levels in the signal processing unit 13 to determine the presence/absence of the defects 6 and 7.

Figure 7:
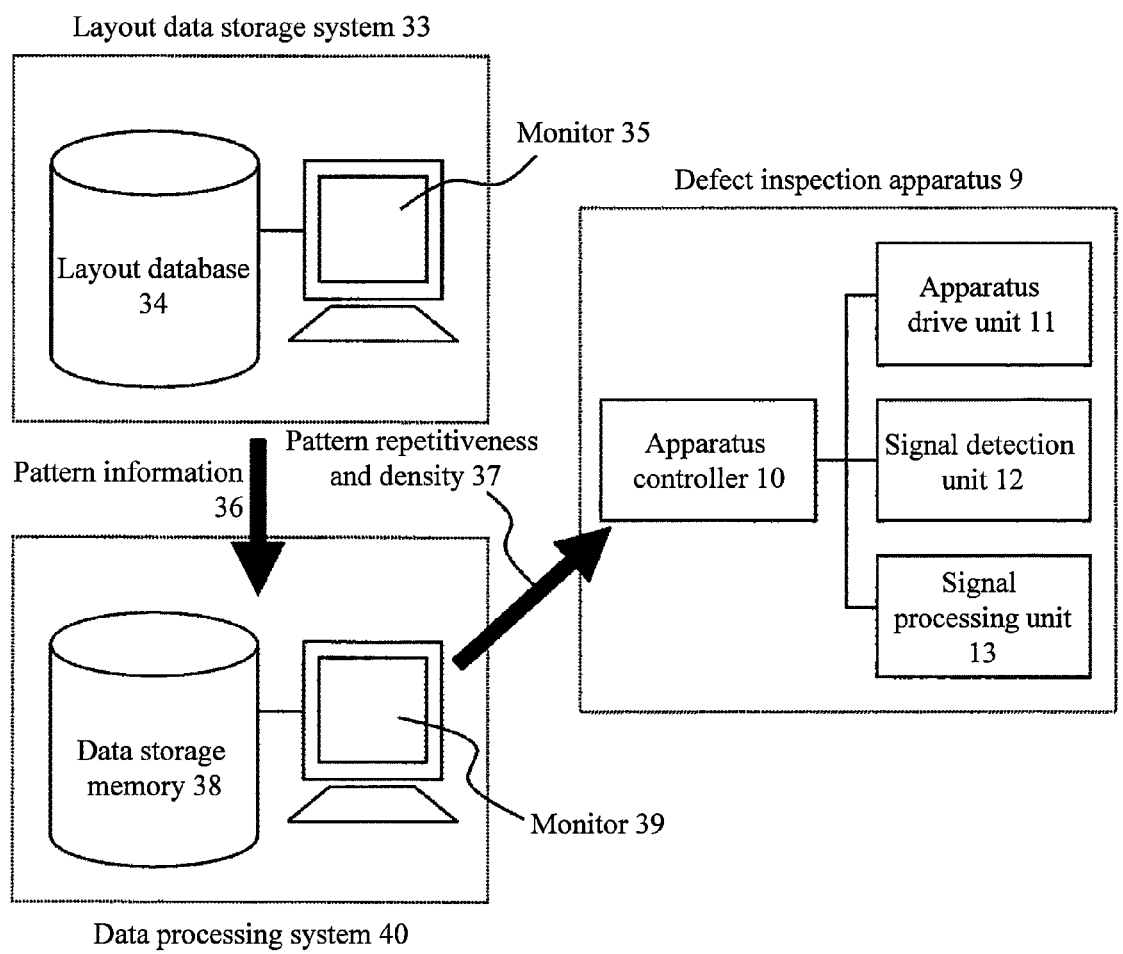
FIG. 7 is a schematic configuration diagram of a defect inspection system according to the present invention.

FIG. 7 is a schematic configuration diagram of a defect inspection system according to the present invention. This system is obtained by adding a data processing system 40 to the configuration of FIG. 6. The data processing system 40 includes a data storage memory 38 and a monitor 39 with a microprocessor. Pattern information 36 including the pattern arrangement, pattern configuration and the like in the inspected chip is sent from the layout data storage system 33 to the external data processing system 40. The data processing system 40 determines information on pattern repetitiveness and density 37 based on the pattern information 36. This information is sent to the apparatus controller 10 of the defect inspection apparatus 9. In driving the stage 27 by means of the apparatus drive unit 11 to inspect the inspected area, the spatial filter 20 is effective for a pattern area determined to have a high repetitiveness, so the signal from the high-transmittance section 30 of the detector 31 or 32 illustrated in FIG. 5 is used. For a pattern area determined to have a low repetitiveness, the signal from the low-transmittance section 29 of the detector 31 or 32 is used. These signals are compared with the threshold levels in the signal processing unit 13 to determine the presence/absence of the defects 6 and 7.

Figure 8:
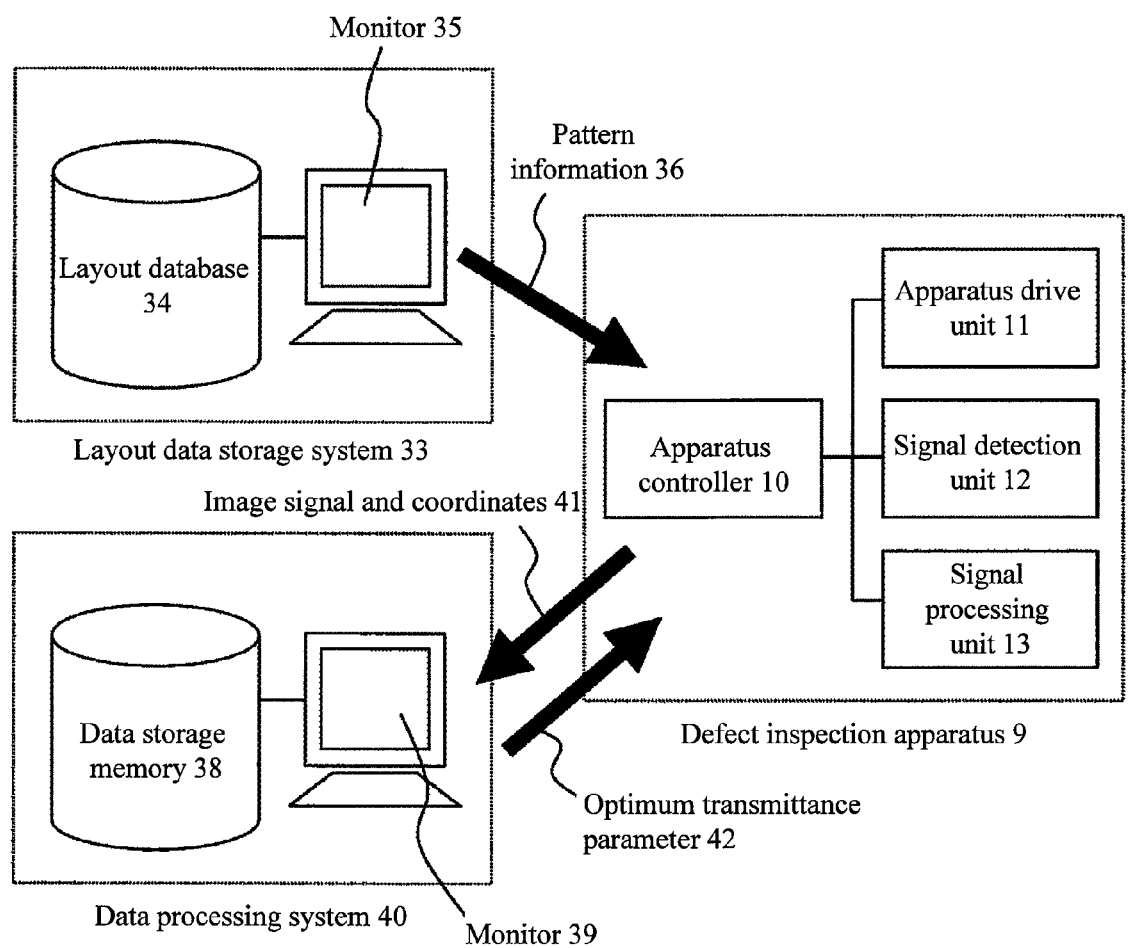
FIG. 8 is a schematic configuration diagram of a defect inspection system according to the present invention.

FIG. 8 is a schematic configuration diagram of a defect inspection system according to the present invention. This system is obtained by adding a data processing system 40 to the configuration of FIG. 6, but the functions of constituent devices are different from those of FIG. 7. The pattern information 36 including the pattern arrangement, pattern configuration and the like in the inspected chip is sent from the layout data storage system 33 to the apparatus controller 10 of the defect inspection apparatus 9. The apparatus controller 10 determines information on pattern repetitiveness and density 37 based on the pattern information 36. In driving the stage 27 by means of the apparatus drive unit 11 to inspect the inspected area, the spatial filter 20 is effective for a pattern area determined to have a high repetitiveness, so the signal from the high-transmittance section 30 of the detector 31 or 32 illustrated in FIG. 5 is used. For a pattern area determined to have a low repetitiveness, the signal from the low-transmittance section 29 of the detector 31 or 32 is used. These signals are compared with the threshold levels in the signal processing unit 13 to determine the presence/absence of the defects 6 and 7. The inspection for each inspected area is performed using multiple transmittance values, and the image signal and coordinates information 41 of a defect candidate is sent to the external data processing system 40. The data processing system 40 determines an optimum transmittance condition based on a combination of the multiple transmittance values and the number of defect candidates. The determination of transmittance will be described later with reference to FIG. 10.

Figure 9:
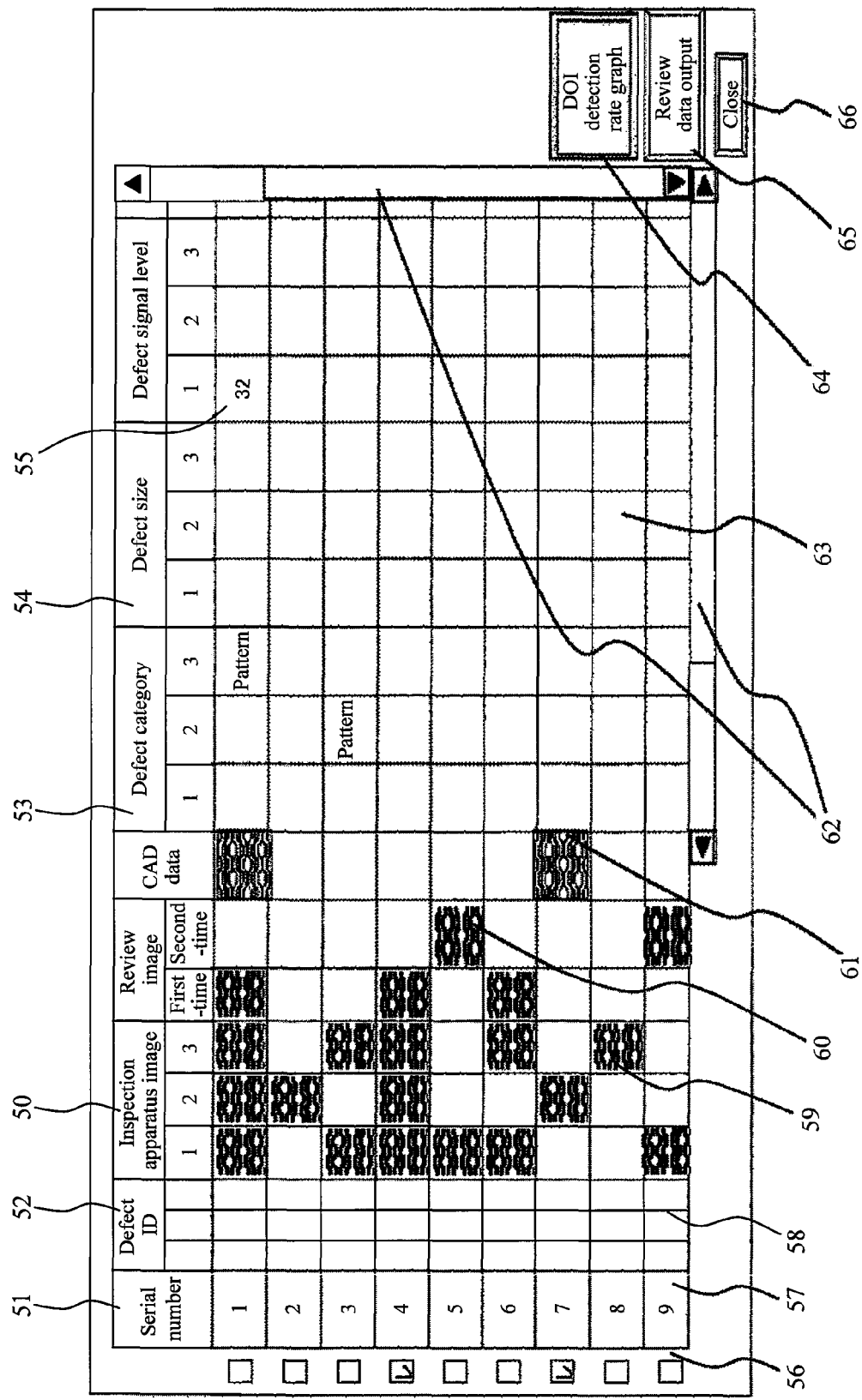
FIG. 9 is a user interface screen view displayed on a monitor of a data processing system.

FIG. 9 is a user interface screen view displayed on the monitor 39 of the data processing system 40. There will be described below: the content of processing inspection data including defect feature quantity and image data outputted from the defect inspection apparatus 9; and the method of displaying the inspection data.

An icon on the desk top of the data processing system 40 is double-clicked to start up the data processing system, so that a screen 50 illustrated in FIG. 9 is displayed on the monitor 39. As a result of being associated with corresponding coordinates data, the following pieces of information are displayed in parallel on the screen 50: multiple images 59 sent from the defect inspection apparatus when the inspection is performed by varying the transmittance; feature quantity data 55 including transmittance parameter setting and the luminance of defect part; multiple ADR images 60 and ADC information 63 sent from a review apparatus (not illustrated); and CAD data image 61 clipped at a given location from layout data sent from the layout database 34. A scroll bar 62 is displayed depending on the number of coordinates data, so that information corresponding to given coordinates can be displayed. In each column, each information can be displayed in ascending order or in descending order by clicking on the title sections 51, 52, 53 and 54.

Multiple inspection data displayed on the screen 50 each have defect ID 58. However, defect ID 58 is assigned during inspection independently of the data processing and thus is meaningless during the analysis by the screen 50. Accordingly, serial number 57 is automatically assigned in addition to defect ID 58, so that all the data inputted to the data processing system can be managed using serial number 57. Further, on the screen 50, the titles for the three inspection conditions, image data corresponding to two reviews, CAD data, and ADC result 53 is displayed so that these data can be perceived. A defect contained in a review file sent to the review apparatus can be arbitrarily selected by ticking a defect selection section 56 and then clicking a review data output button 65.

Figure 10:
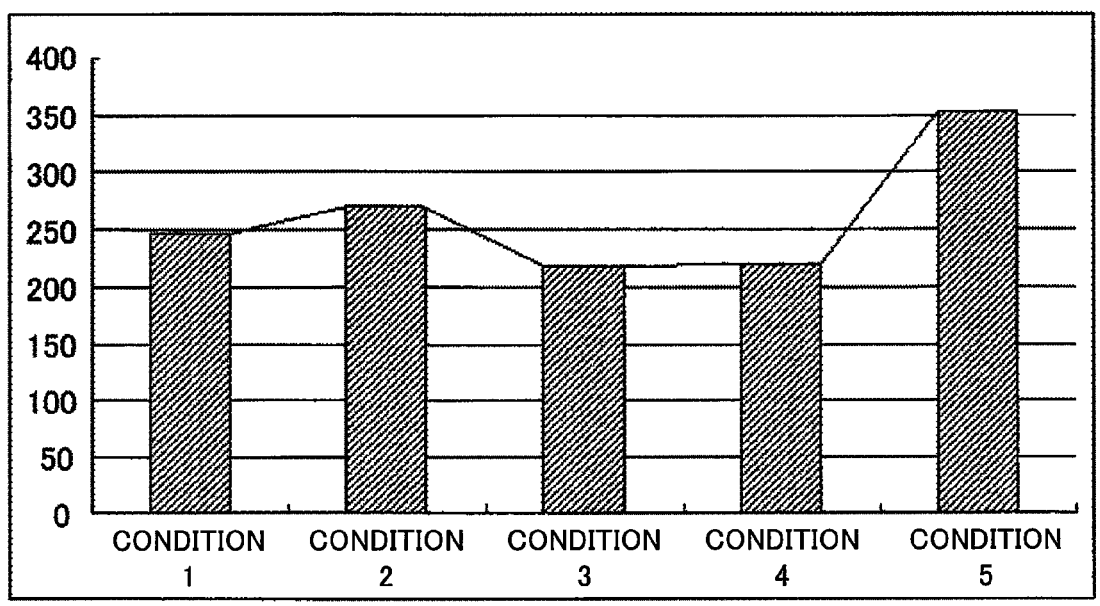
FIG. 10 is a graph illustrating the number of DOI defects detected under five inspection conditions.

FIG. 10 is a graph illustrating the number of DOI defects detected under five inspection conditions. The number of inspection conditions is three in FIG. 9 but in this case, the number is set to five and after the screen 50 is displayed, a DOI inspection rate graph button is clicked, whereby the screen of FIG. 10 is displayed. DOI (Defect Of Interest) means a defect in which the operator of the data processing system has an interest. In the example of FIG. 10, a largest number of DOIs are detected under condition 5. That is, the transmittance value used at condition 5 is the optimum setting. In this case, the relationship between the DOI at condition 5 and the degradation of product yield ratio can be checked using defect images and ADC results displayed on the screen 50 illustrated in FIG. 9. The optimum transmittance parameter 42 thus selected is, as illustrated in FIG. 8, sent from the data processing system 40 to the apparatus controller 10 of the defect inspection apparatus 9.

Figure 11:
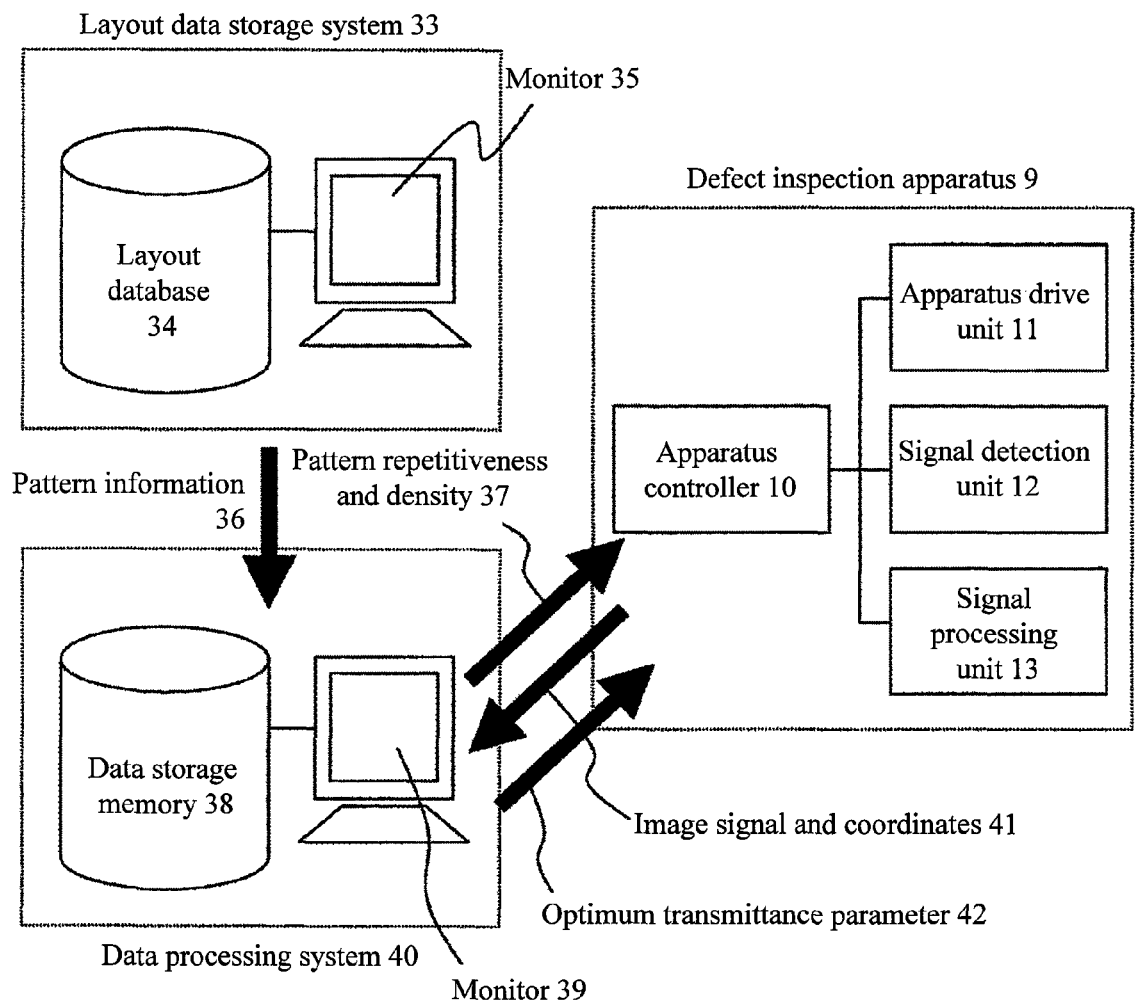
FIG. 11 is a schematic configuration diagram of a defect inspection system according to the present invention.

FIG. 11 is a schematic configuration diagram of a defect inspection system according to the present invention. The data communication content between the data processing system 40 and defect inspection apparatus 9 in the system of FIG. 11 is different from that of FIG. 7. Pattern information 36 including the pattern arrangement, pattern configuration and the like in the inspected chip is sent from the layout data storage system 33 to the data processing system 40. The data processing system 40 determines information on pattern repetitiveness and density 37 based on the pattern information 36. This information is sent to the apparatus controller 10 of the defect inspection apparatus 9. In driving the stage 27 by means of the apparatus drive unit 11 to inspect the inspected area, the spatial filter 20 is effective for a pattern area determined to have a high repetitiveness, so the signal from the high-transmittance section 30 of the detector 31 or 32 illustrated in FIG. 5 is used. For a pattern area determined to have a low repetitiveness, the signal from the low-transmittance section 29 of the detector 31 or 32 is used. These signals are compared with the threshold levels in the signal processing unit 13 to determine the presence/absence of the defects 6 and 7. The inspection for each inspected area is performed using multiple transmittance values, and the image signal and coordinates information 41 of a defect candidate is sent to the external data processing system 40. The data processing system 40 determines an optimum transmittance condition based on a combination of the transmittance values and the number of defect candidates. The transmittance parameter 42 determined to be optimum is sent to the apparatus controller 10 of the defect inspection apparatus 9. Here, "optimum transmittance" means, as described with reference to FIG. 10, a transmittance with which the number of DOIs is largest.

Figure 12:
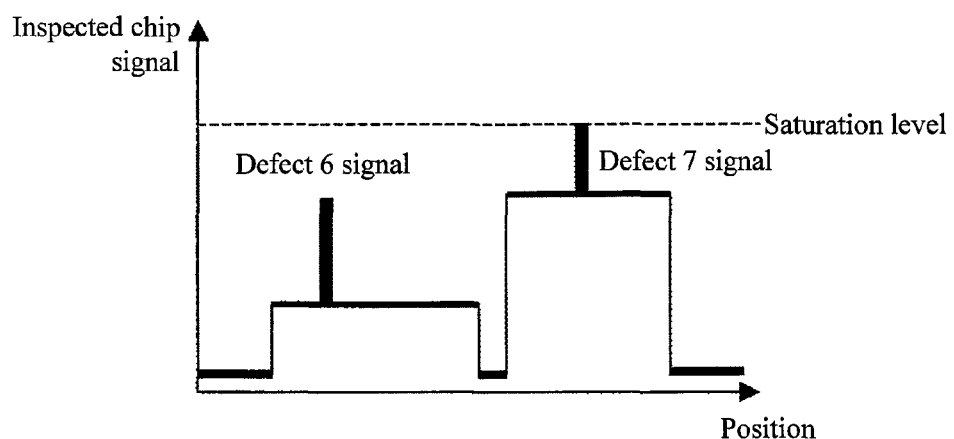
FIG. 12 is a graph illustrating a signal level at the A scan cross-section of FIG. 2.
Figure 12:
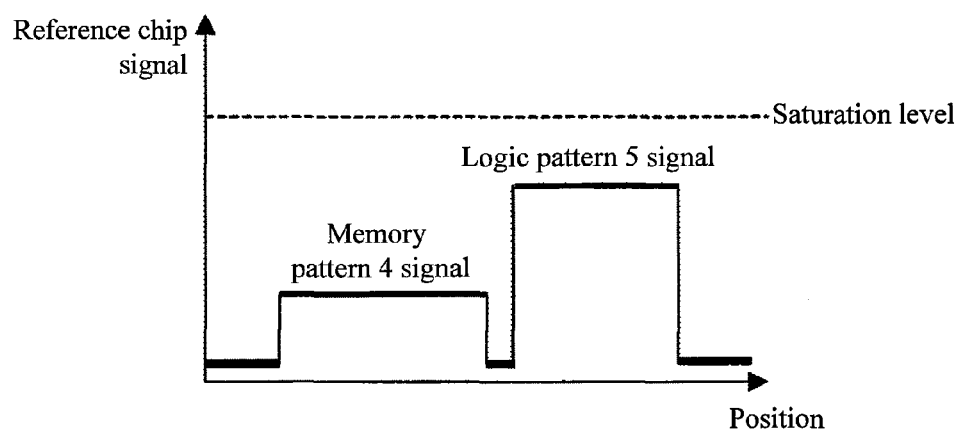
Figure 12:
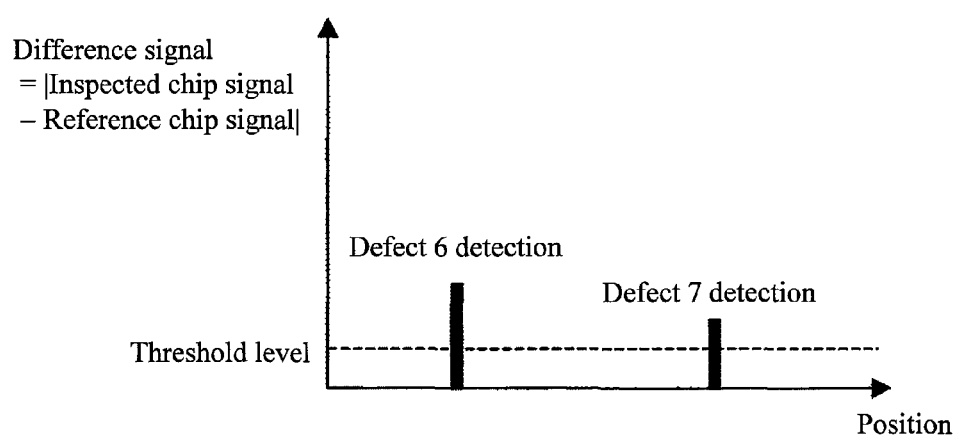

FIG. 12 is a graph illustrating a signal level at the A scan cross-section of FIG. 2; the position is plotted along the abscissa and the signal level along the ordinate. Signal saturation can be prevented by optimizing the transmittance depending on the pattern, so there can also be detected the defect 7 of the logic section illustrated in FIG. 2 which cannot be detected according to the related art. Referring to FIG. 12(A), the inspected chip signal is plotted along the ordinate, whereby the signal level at the A scan cross-section of FIG. 2 is illustrated. According to the related art illustrated in FIG. 4(A), the signal from the logic pattern 5 of the logic section of FIG. 2 exceeds the saturation level, so the defect 7 cannot be detected. However, when the signal detection is performed under the optimum transmittance condition, as illustrated in FIG. 12(A), the signal from the logic pattern 5 of the logic section of FIG. 2 does not exceed the saturation level, so the signal from the defect 7 appears. Referring to FIG. 12(B), the reference chip signal is plotted along the ordinate. According to the related art illustrated in FIG. 4(B), the signal from the logic pattern 5 of the logic section of FIG. 2 exceeds the saturation level. However, when the signal detection is performed under the optimum transmittance condition, as illustrated in FIG. 12(B), the signal from the logic pattern 5 of the logic section of FIG. 2 does not exceed the saturation level. Referring to FIG. 12(C), plotted along the ordinate is a difference signal, i.e., a difference between the inspected chip signal of FIG. 12(A) and the reference chip signal of FIG. 12(B). According to the related art illustrated in FIG. 4(C), the defect 6 of the memory section 2 of FIG. 2 can be detected, but the defect 7 of the logic section cannot be detected. In contrast, referring to FIG. 12(C), since the signal detection is performed under the optimum transmittance condition, so that the signal from the logic pattern 5 of the logic section does not reach the saturation level, when the difference between the signal of FIG. 12(A) and the signal of FIG. 12(B) is calculated, the signal from the defect 7 appears; when this signal exceeds the threshold level as illustrated in FIG. 12(C), the defect 7 can be detected.

As described above, according to the present embodiment, the signal detection can be performed using, depending on the design layout data of semiconductor pattern, the level at which detected signal saturation does not occur. Thus, defects in the logic pattern can be unfailingly detected. As a result, the investigation of the cause for defect occurrence in the logic pattern can be started earlier, thus contributing to product yield rate improvement. Further, with the same inspected object, even when the defect detection sensitivity varies depending on individual characteristics of defect inspection apparatuses, proper adjustments can be made so that the defect detection is performed at the same level; thus in performing the defect inspection using multiple defect inspection apparatuses, inspection level equalization can be done. Further, in setting the inspection condition, the condition corresponding to the optimum signal transmittance can be easily determined, thus shortening the length of time taken to set the inspection condition.

What is claimed is:

1. A defect inspection method comprising:
   irradiating light on an object to be inspected having a pattern formed thereon;
   detecting a signal from the object;
   processing the detected signal to detect a defect;
   inputting pattern information contained in layout data of the object;
   acquiring, based on the inputted pattern information, repetitiveness for each of a plurality of inspected areas of the object;
   acquiring a saturation level of the detected signal based on the repetitiveness; and
   determining a transmittance condition so that the detected signal does not reach the saturation level.

2. The defect inspection method according to claim 1, wherein
   a plurality of inspection conditions are used to detect the defect, and
   a transmittance condition corresponding to an inspection condition under which the number of detected defects is largest is selected based on the transmittance condition.

3. The defect inspection method according to claim 2, wherein the plurality of the inspection conditions includes at least one of information on the inspected object, the power of the laser light, spatial filter, and the transmittance of a variable-transmittance filter.

4. The defect inspection method according to claim 1, further comprising acquiring at least of one of arrangement and density, wherein the saturation level of the detected signal is determined based on the acquired at least one of arrangement and density, in addition to the repetitiveness.

5. A defect inspection system comprising:
   a storage device which stores pattern information contained in layout data of an object to be inspected;
   an irradiation device which irradiates light on the object having a pattern formed thereon;
   a processing device which acquires repetitiveness on the basis of the pattern information; and
   a detection device which detects light from the object, wherein the detection device changes the intensity of light from the object based on the repetitiveness.

6. The defect inspection system according to claim 5, wherein the pattern information is information about a pattern form.

7. The defect inspection system according to claim 5, wherein the pattern information is information about a pattern arrangement.

8. The defect inspection system according to claim 5, wherein:
   the processing device is coupled to the storage device and the detection device,
   the processing device reads out the pattern information from the storage device and acquires the repetitiveness and at least one of arrangement and density for each of inspection areas of the object based on the pattern information; and
   the detection device changes the intensity of light from the object based on the repetitiveness and at least one of the arrangement and density.

9. The defect inspection system according to claim 5, further comprising:
   an inspection apparatus; and
   a network, wherein:
   the irradiation device and the detection device are included in the inspection apparatus and,
   the inspection apparatus is coupled to the storage device through the network.

10. The defect inspection system according to claim 5, wherein:
   the detection devices includes a sensor which generates a detection signal;

the defect inspection system further comprises a filter which covers a part of the sensor, wherein a transmittance rate of filtered area by the filter is lower than a transmittance rate of non-filtered area; and the detection device uses the filtered area or the non-filtered area as a function of the repetitiveness.

* * * * *